US00PP27971P2

(12) United States Plant Patent
van den Hoogen

(10) Patent No.: US PP27,971 P2
(45) Date of Patent: May 2, 2017

(54) ***HYPERICUM* PLANT NAMED 'ALLBOO'**

(50) Latin Name: *Hypericum hybrida*
Varietal Denomination: Allboo

(71) Applicant: ALLPLANTS HOLDING B.V., Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 14/998,486

(22) Filed: Jan. 9, 2016

(51) Int. Cl.
*A01H 5/02* (2006.01)

(52) U.S. Cl.
USPC ..... Plt./442

(58) Field of Classification Search
USPC ..... Plt./442, 226
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hypericum* plant named 'Allboo', characterized by its broadly upright plant habit; moderately vigorous growth habit; dark green-colored leaves; freely flowering habit and high fruit density; glossy bright green-colored fruits; and suitability as a cut-flower plant.

3 Drawing Sheets

Botanical designation: *Hypericum hybrida.*
Cultivar denomination: 'ALLBOO'.

BACKGROUND OF THE INVENTION

The present invention relates to a new and distinct cultivar of *Hypericum* plant, botanically known as *Hypericum hybrida*, typically grown as a cut-flower plant and hereinafter referred to by the name 'Allboo'.

The new *Hypericum* plant is a product of a planned breeding program conducted by the Inventor in Cuijk, The Netherlands. The objective of the breeding program is to create new *Hypericum* plants with strong stems, numerous attractive fruits and good postproduction longevity.

The new *Hypericum* plant originated from an open-pollination in September, 2011 in Cuijk, The Netherlands of a proprietary selection of *Hypericum hybrida* identified as code number C10-145, not patented, as the female, or seed parent with an unknown selection of *Hypericum hybrida* as the male, or pollen, parent. The new *Hypericum* plant was discovered and selected by the Inventor as a single flowering plant from within the progeny of the stated open-pollination in a controlled outdoor nursery environment in Cuijk, The Netherlands in September, 2012.

Asexual reproduction of the new *Hypericum* plant by vegetative cuttings in a controlled outdoor nursery environment in Cuijk, The Netherlands since September, 2012 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allboo'. These characteristics in combination distinguish 'Allboo' as a new and distinct *Hypericum* plant:

1. Broadly upright plant habit.
2. Moderately vigorous growth habit.
3. Dark green-colored leaves.
4. Freely flowering habit and high fruit density.
5. Glossy bright green-colored fruits.
6. Suitable as a cut-flower plant.

Plants of the new *Hypericum* differ primarily from plants of the female parent selection in the following characteristics:

1. Leaves of plants of the new *Hypericum* have obtuse apices whereas leaves of plants of the female parent selection have acute apices.
2. Plants of the new *Hypericum* produce larger fruits than plants of the female parent selection.
3. Plants of the new *Hypericum* and the female parent selection differ in fruit color as plants of the female parent selection produce light yellow green-colored fruits.

Plants of the new *Hypericum* can be compared to plants of the *Hypericum hybrida* 'Allbam', not patented. In side-by-side comparisons, conducted in Cuijk, The Netherlands, plants of the new *Hypericum* differed primarily from plants of 'Allbam' in the following characteristics:

1. Leaves of plants of the new *Hypericum* had obtuse apices whereas leaves of plants of 'Allbam' had acute apices.
2. Plants of the new *Hypericum* and 'Allbam' differed in fruit color as plants of 'Allbam' produced light green-colored fruits.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet is a side perspective view of a flowering plant of 'Allboo' grown in a container.

The photograph on the second sheet is a close-up view of a typical stem and leaves of 'Allboo'.

The photograph on the third sheet is a close-up view of a typical plant of 'Allboo' with mature fruits.

DETAILED BOTANICAL DESCRIPTION

Plants used for the aforementioned photographs and following description were grown in September in an outdoor nursery in Cuijk, The Netherlands and under cultural practices typical of commercial cut-flower *Hypericum* production. During the production of the plants, day temperatures ranged from 13° C. to 26° C. and night temperatures ranged from 6° C. to 16° C. Plants were seven months old when the photographs and description were taken. In the following description, color references are made to The Royal Horticultural Society Colour Chart, 2015 Edition, except where general terms of ordinary dictionary significance are used.

Botanical classification: *Hypericum hybrida* 'Allboo'.

Parentage:

*Female, or seed, parent*.—Proprietary selection of *Hypericum hybrida* identified as code number C10-145, not patented.

*Male, or pollen, parent*.—Unknown selection of *Hypericum hybrida*, not patented.

Propagation:

*Type cutting*.—Vegetative cuttings.

*Time to initiate roots, summer*.—About 10 to 14 days at temperatures about 12° C. to 30° C.

*Time to initiate roots, winter*.—About 14 to 20 days at temperatures about 12° C. to 22° C.

*Time to produce a rooted young plant, summer*.—About 24 to 32 days at temperatures ranging from 12° C. to 30° C.

*Time to produce a rooted young plant, winter*.—About 28 to 36 days at temperatures ranging from 12° C. to 22° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Perennial shrub; broadly upright plant habit; moderately vigorous growth habit.

*Branching habit*.—Moderately freely basal branching habit; pinching enhances lateral branch development.

*Plant height*.—About 59 cm.

*Plant width* (*spread*).—About 35 cm.

*Lateral branch description*.—Length: About 21.9 cm. Diameter: About 4 mm. Internode length: About 4.9 cm. Strength: Moderately strong to strong. Texture and luster: Smooth, glabrous; moderately glossy. Color, developing: Close to 144B strongly tinged with close to 176A. Color, fully developed: Close to N199A and 200D.

Leaf description:

*Arrangement*.—Opposite, simple; sessile.

*Length*.—About 7.3 cm.

*Width*.—About 5 cm.

*Shape*.—Broadly ovate.

*Apex*.—Obtuse to very slightly retuse.

*Base*.—Truncate.

*Margin*.—Entire.

*Texture and luster, upper and lower surfaces*.—Smooth to slightly rugose; glabrous; slightly glossy.

*Venation pattern*.—Pinnate.

*Color*.—Developing leaves, upper surface: Close between 144A and 146B. Developing leaves, lower surface: Close to 146C to 146D moderately tinged with close to 152B. Fully expanded leaves, upper surface: Darker than between NN137A and 139A; venation, close to 144B. Fully expanded leaves, lower surface: Close to between 138B and 147B; venation, close to 144D.

Flower description:

*Flower type, arrangement and flowering habit*.—Single rotate flowers arranged in terminal and axillary compound cymes; freely flowering habit with about seven flowers per cyme and about 200 flowers developing per plant; flowers face mostly upright.

*Fragrance*.—None detected.

*Natural flowering season*.—Plants flower continuously from late June to early September in The Netherlands.

*Flower longevity*.—Flowers last about two or three days on the plant; flowers not persistent.

*Fruit longevity* (*postproduction*).—About 30 days.

*Flower buds*.—Length: About 9 mm. Diameter: About 9 mm. Shape: Broadly obovate. Color: Close to 12A; towards the apex, close to 13B.

*Inflorescence height*.—About 5.6 cm.

*Inflorescence diameter*.—About 9.3 cm.

*Flower diameter*.—About 3 cm.

*Flower depth* (*height*).—About 2 cm.

*Petals*.—Quantity and arrangement: Five in a single whorl. Length: About 1.4 cm. Width: About 1.1 cm. Shape: Broadly obovate, concave. Apex: Acute. Base: Attenuate. Margin: Entire. Texture, upper and lower surfaces: Smooth, glabrous. Luster, upper surface: Matte. Luster, lower surface: Moderately glossy. Color: When opening and fully opened, upper surface: Close to 13A; color becoming closer to 14B with development. When opening and fully opened, lower surface: Close to 12A; towards the margins, close to 13A.

*Sepals*.—Quantity and arrangement: Five in a single whorl. Length: About 1.4 cm. Width: About 1.1 cm. Shape: Broadly ovate; slightly reflexed. Apex: Broadly acute. Base: Broadly cuneate. Margin: Entire. Texture, upper and lower surfaces: Smooth, glabrous. Luster, upper and lower surfaces: Dull. Color: When opening and fully opened, upper surface: Slightly darker than 143A. When opening and fully opened, lower surface: Close to 144B; distally at the margins, close to 179A.

*Peduncles*.—Length: About 2.1 cm. Diameter: About 1.75 mm. Texture: Smooth, glabrous. Strength: Moderately strong. Aspect: Erect to about 45° from vertical. Color: Close to 144B and 146C; upper surface, slightly tinged with close to 176C.

*Pedicels*.—Length: About 2.4 cm. Diameter: About 1.5 mm. Texture: Smooth, glabrous. Strength: Moderately strong. Aspect: Erect to about 45° from vertical. Color: Close to 144B.

*Reproductive organs*.—Stamens: Quantity per flower: About 100. Filament length: About 1.3 mm. Filament color: Close to 13A. Anther length: About 0.5 mm. Anther shape: Broadly oval; dorsifixed. Anther color: Close to 22A. Pollen amount: Moderate. Pollen color: Close to 15A. Pistils: Quantity per flower: Single pistil with three stigmas. Pistil length: About 3 mm. Stigma shape: Club-shaped. Stigma color: Close to 37A. Style length: About 2.5 mm. Style color: Close to 150B. Ovary color: Close to between N144B and 150B.

*Fruits*.—Quantity per plant: About 200. Length: About 1.4 cm. Diameter: About 1.3 cm. Shape: Spherical. Texture: Smooth, glabrous. Luster: Glossy. Color: Close to 144A.

*Seeds*.—Length: About 0.9 mm. Diameter: About 0.5 mm. Color: Close to 200A.

Disease & pest resistance: Plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'Allboo' as illustrated and described.

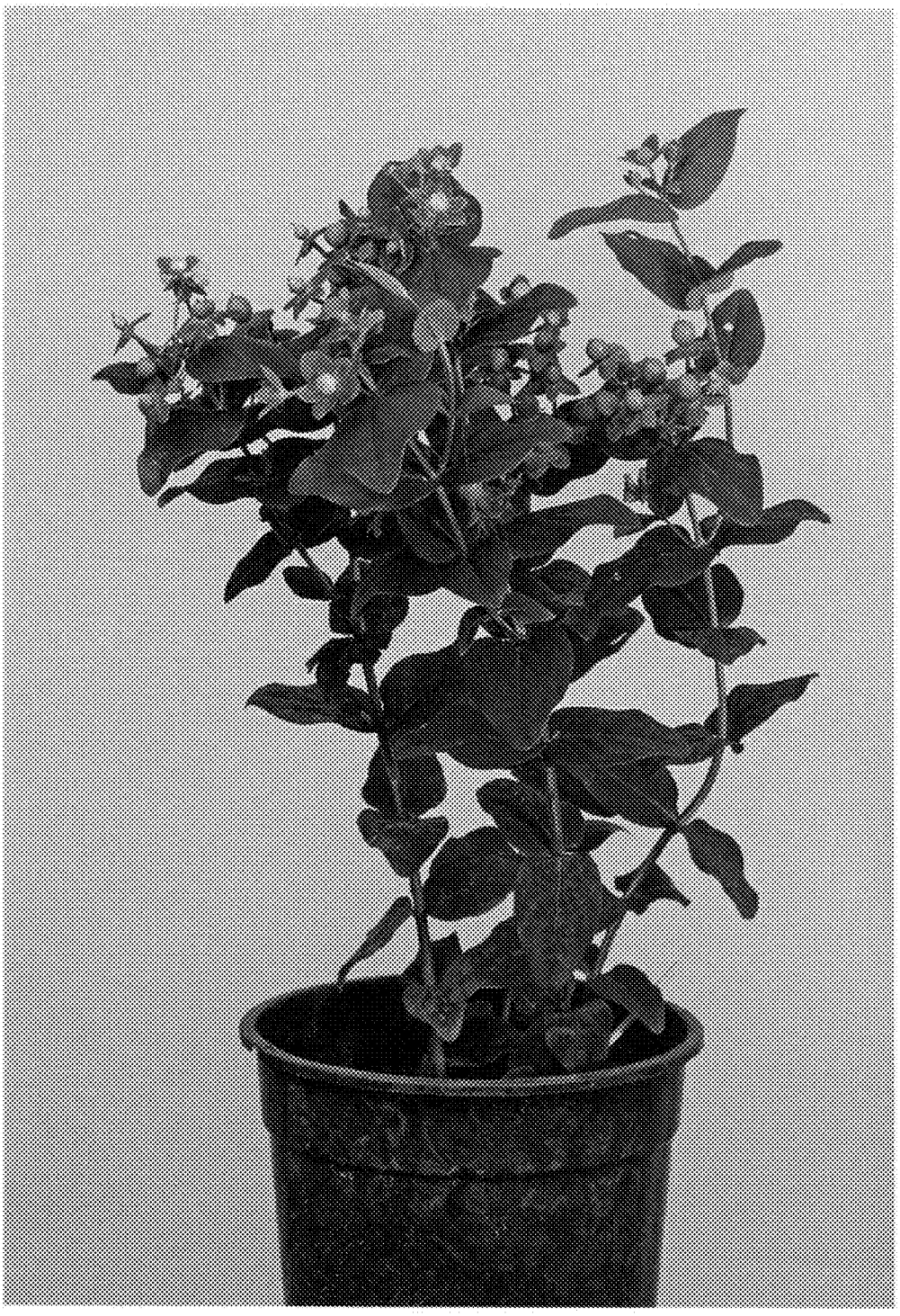

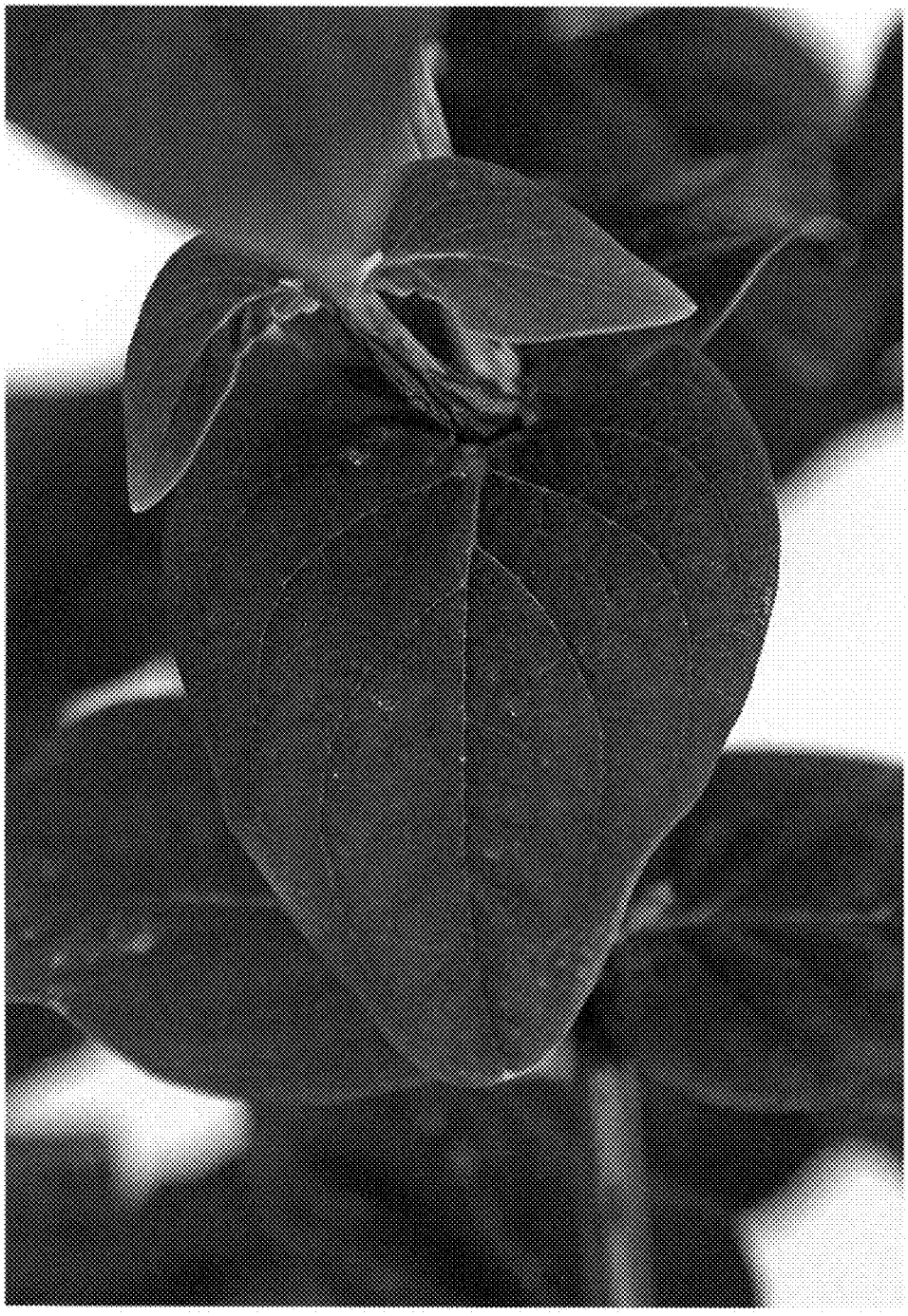

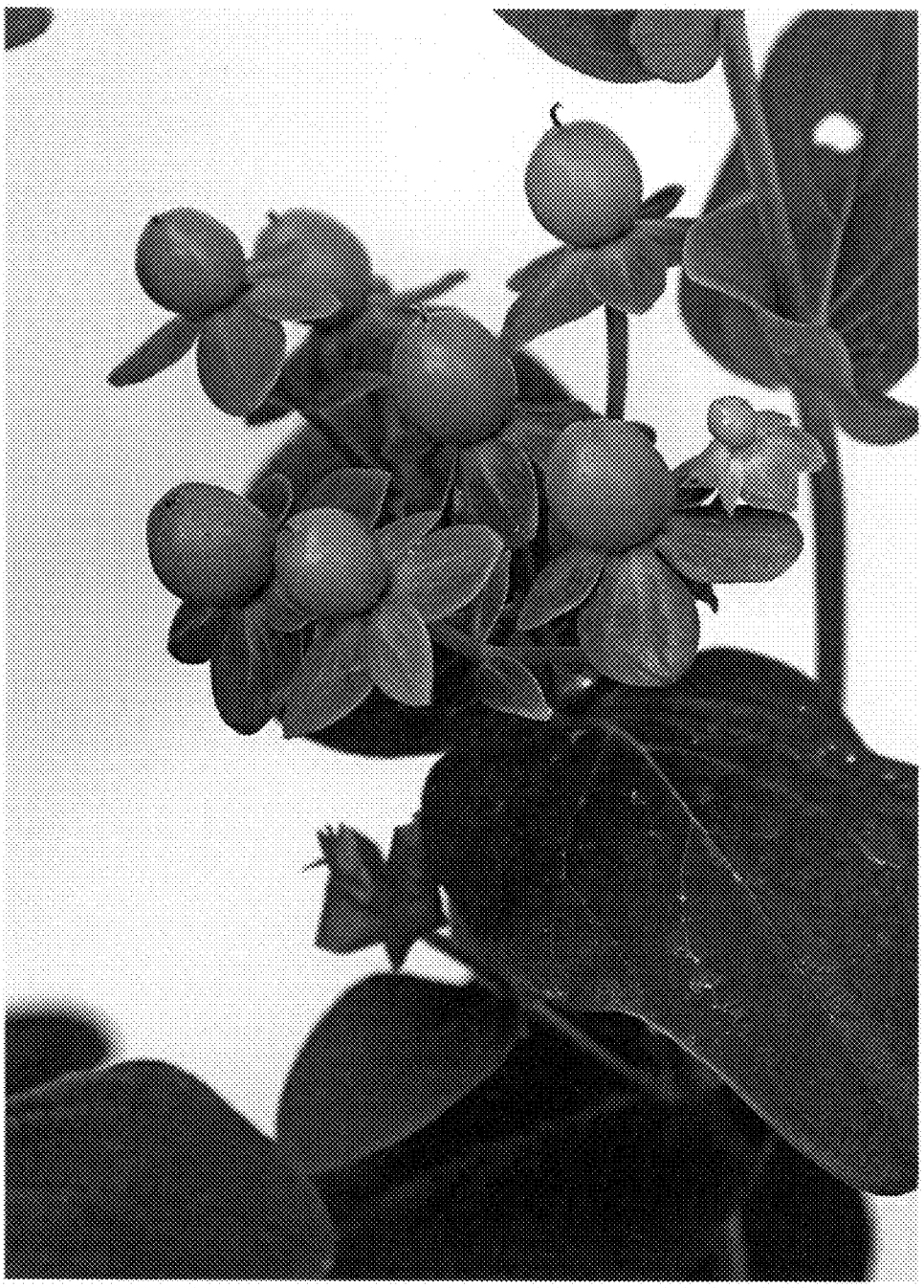

* * * * *